United States Patent [19]

Cragoe, Jr. et al.

[11] 4,349,561

[45] Sep. 14, 1982

[54] 4-SUBSTITUTED-3-HYDROXY-3-PYRROLINE-2,5-DIONE INHIBITORS OF GLYCOLIC ACID OXIDASE

[75] Inventors: Edward J. Cragoe, Jr., Lansdale; Clarence S. Rooney, Worcester, both of Pa.; Haydn W. R. Williams, Dollard des Ormeaux, Canada

[73] Assignee: Merck & Co., Inc., Rahway, N.J.

[21] Appl. No.: 91,293

[22] Filed: Nov. 5, 1979

[51] Int. Cl.$^3$ ..................... A61K 31/40; C07D 207/26
[52] U.S. Cl. ............................ 424/274; 260/326.5 R; 260/326.5 C; 260/326.5 CA; 560/56; 564/180
[58] Field of Search .............. 260/326.5 C, 326.5 CA; 424/274

[56] References Cited

U.S. PATENT DOCUMENTS 3,340,263 9/1967 Stachella ............................ 260/268

OTHER PUBLICATIONS

Ligo et al., "Arch. Biochem. Biophys", vol. 154, (1973), pp. 68–75.
Harlay, "J. Pharm. Chim.", vol. 24, (1936), pp. 537–548.
Skinner et al., "J. Am. Chem. Soci.", vol. 73, (1951), p. 2230.
Skinner, "JACS", vol. 70, (1948), p. 4011.

*Primary Examiner*—Anton H. Sutto
*Attorney, Agent, or Firm*—Raymond M. Speer; Michael C. Sudol, Jr.

[57] ABSTRACT

Novel 4-substituted-3-hydroxy-3-pyrroline-2,5-diones are disclosed which inhibit glycolic acid oxidase and thus are useful in the treatment and prevention of calcium oxalate kidney stone formation. A novel process for their preparation is also disclosed.

9 Claims, No Drawings

4-SUBSTITUTED-3-HYDROXY-3-PYRROLINE-2,5-DIONE INHIBITORS OF GLYCOLIC ACID OXIDASE

BACKGROUND OF THE INVENTION

Close to 70% of kidney stones in man are composed partially or predominantly of calcium oxalate. There is no satisfactory drug specific for the treatment of calcium oxalate renal lithiasis, nor for prophylactic use by patients prone to recurrent attacks of this disease.

The most common treatment for renal lithiasis due to calcium oxalate consists of surgical removal of stones, control of the diet to restrict calcium or oxalate, and ingestion of large quantities of water to dilute the urine. Attempts at chemotherapy have included the administration of magnesium oxide, calcium carbimide, orthophosphate, cellulose phosphate, isocarboxazide, thiazide diuretics, allopurinol and succinimide. Limited success has been realized by these drug approaches. No drug which specifically inhibits the biosynthetic formation of oxalic acid has previously been developed for the treatment of calcium oxalate renal lithiasis.

The immediate metabolic precursor of the majority of the oxalate in the urine of a typical patient is glyoxylic acid. In turn its most important precursor is glycolic acid. The enzyme glycolate oxidase is able to carry out the oxidation of glycolic acid, through glyoxylic acid, to oxalic acid. Inhibition of this enzyme will, therefore, reduce the concentration of oxalic acid in the kidney and bladder, decreasing the probability that calcium oxalate crystallization will occur. Thus inhibitors of glycolate oxidase provide a specific approach to the prevention and treatment of calcium oxalate renal lithiasis.

Liao, et al, *Arch. Biochem. Biophys.*, 154, 68–75 (1973) have shown that phenyllactic acid and n-heptanoic acid, which are inhibitors of glycolate oxidase, inhibit oxalate biosynthesis in isolated perfused rat liver. These compounds are not sufficiently potent to be useful as drugs.

The preparation of 3-hydroxy-4-phenyl-3-pyrroline-2,5-dione

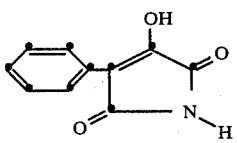

has been described by Harlay, *J. Pharm. Chim.*, 24, 537-48 (1936). 3-Hydroxy-4-aryl-3-pyrroline-2,5-diones are described in U.S. Pat. No. 3,349,263 as intermediates in the preparation of antiphlogistic substances.

A number of 3-hydroxy-4-substitutedphenyl-3-pyrroline-2,5-diones are reported by G. S. Skinner, et al., *J. Am. Chem. Soc.*, 73, 2230 (1951). (In this paper these compounds are referred to as pyrrolidine-2,3,5-trione derivatives). 3-Hydroxy-4-(4-bromo-1-naphthyl)-3-pyrrolidine-2,5-dione is described by G. S. Skinner, et al., *J. Am. Chem Soc.*, 70, 4011(1948).

Compounds of the structure

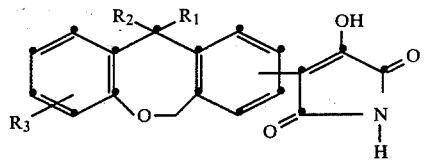

and

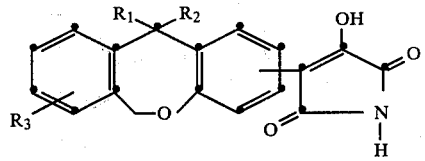

are disclosed in a previous patent application by J. Rokach, E. J. Cragoe, Jr. and C. S. Rooney now U.S. Ser. No. 930,103, filed Aug. 1, 1978, now abandoned, where these preparations are also described. Compounds of this type are covered in this invention only by the method of use claim (i.e. just claims to use for renal lithiasis).

SUMMARY OF THE INVENTION

It has now been found that compounds of the formula:

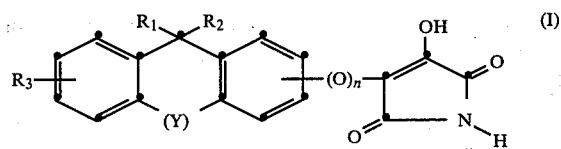

wherein
n is 0 or 1;
Y is $CH_2-CH_2$; $CH=CH$; $CH_2-O$; $O-CH_2$;
$R_1$ and $R_2$ are both hydrogen, hydrogen and hydroxyl or taken together are =O;
$R_3$ is hydrogen or halogen; particularly compounds having the structure

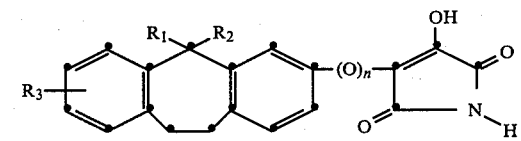

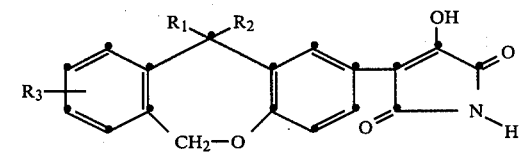

and

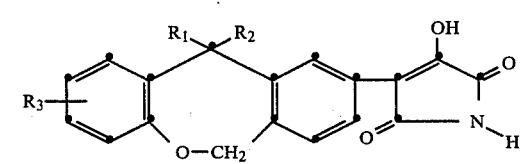

wherein n is 0 or 1;

the dotted line indicates saturation or unsaturation;

$R_1$ and $R_2$ are both hydrogen, hydrogen and hydroxyl or taken together are =O;

$R_3$ is hydrogen or halogen and compounds having the structural formula:

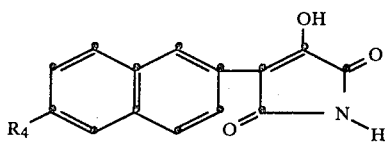

wherein $R_4$ is hydrogen, halogen, loweralkoxy containing 1 to 6 carbon atoms or

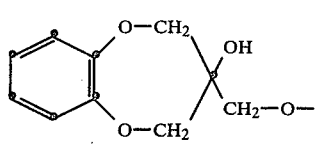

or a pharmaceutically acceptable salt thereof are potent inhibitors of glycolate oxidase. They are, therefore, useful in the treatment and prevention of calcium oxalate kidney and bladder stone formation.

Included in the present invention are novel compounds having the structural formula:

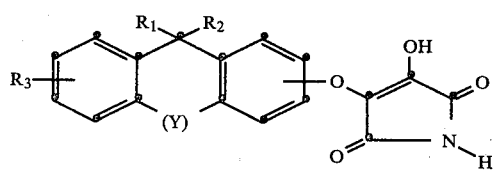

wherein

Y is $CH_2-CH_2$; $CH=CH$; $CH_2-O$; $O-CH_2$;

$R_1$ and $R_2$ are both hydrogen, hydrogen and hydroxyl or taken together are =O;

$R_3$ is hydrogen, or halogen; and particularly those novel compounds wherein

Y is $CH_2-CH_2$; $CH=CH$;

$R_1$ and $R_2$ are both hydrogen, hydrogen and hydroxyl or taken together are =O;

$R_3$ is hydrogen or halogen; having the structural formula:

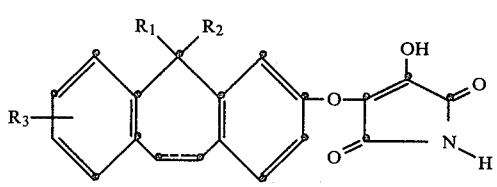

wherein the dotted line indicates saturation or unsaturation.

Also included are novel compounds having the structural formula:

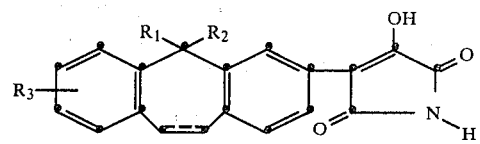

wherein $R_1$ and $R_2$ are both hydrogen, hydrogen and hydroxyl, or taken together are =O;

$R_3$ is hydrogen or halogen.

Other types of novel compounds included in this invention are those with the structural formulae

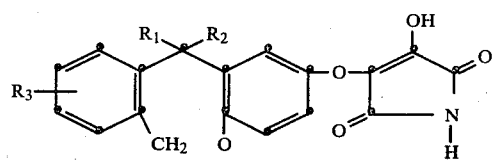

and

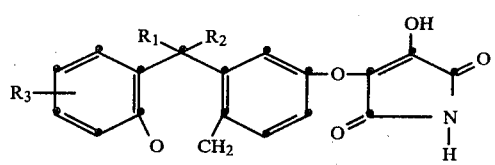

wherein $R_1$ and $R_2$ are both hydrogen, hydrogen and hydroxyl, or taken together are =O; $R_3$ is hydrogen or halogen.

Also included in the present invention are novel compounds having the structural formula:

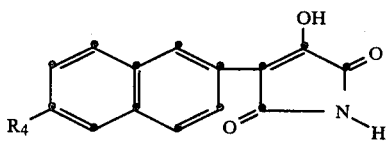

wherein $R_4$ is hydrogen, halogen, loweralkyl containing 1 to 6 carbon atoms or

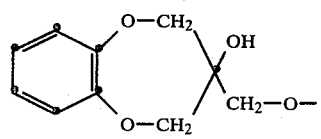

and pharmaceutically acceptable salts thereof.

DETAILED DESCRIPTION

About 70% of all renal calculi contain oxalate as the main component of the matrix. In the majority of patients the condition is associated with a higher than average level of metabolically produced oxalate. The major pathway for biosynthesis of oxalate can be represented as follows:

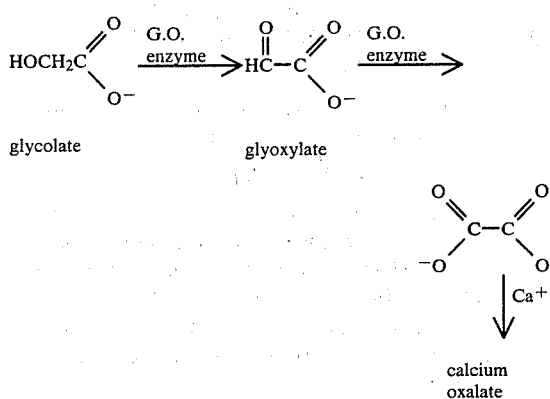

Glyoxylate is the major immediate forerunner of oxalate. An inhibitor of glycolate oxidase (G.O.) will inhibit both the conversion of glyoxylate to oxalate as well as the production of glyoxylate from glycolate. By reducing oxalic acid levels in the urine with the compounds of this invention, the formation of oxalate calculi will be reduced or prevented.

Compounds of formula (I) are potent inhibitors of glycolate oxidase and thus are useful in restricting oxalate levels in the blood and urine. Further, they are useful in the treatment and prevention of renal disease due to calcium oxalate stone formation in the kidney and bladder. They may also be useful in the treatment of the genetically inherited diseases termed Hyperoxaluria types I and II.

Compounds of formula (I) have been unexpectedly found to block the contractions of guinea pig ileum induced by Slow Reacting Substance of Anaphylaxis (SRS-A). They are ineffective against contractions caused by histamine, which demonstrates specificity against SRS-A. SRS-A is considered a major mediator in human allergic asthma. Thus the compounds of formula (I) are useful in the treatment of allergy, especially allergic asthma.

Compounds of formula (I) can be prepared according to the following routes:

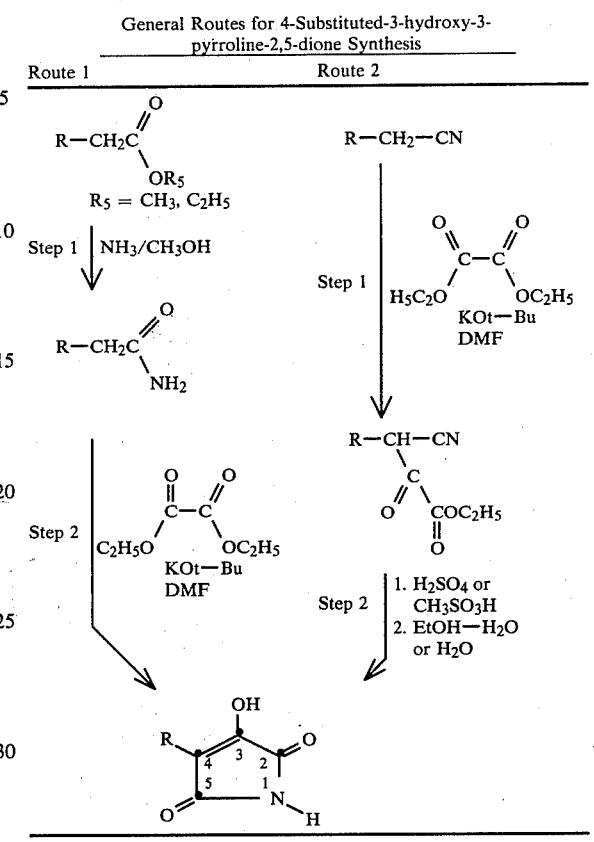

The following general routes to the syntheses of the above ester (or nitrile) intermediates are applicable to compounds of this invention.

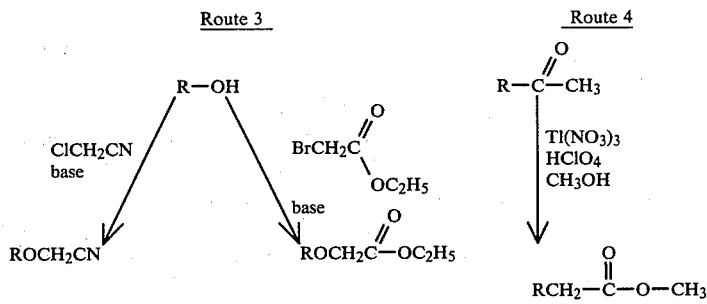

The reactions with ethyl bromoacetate or chloroacetonitrile are applicable to the synthesis of those derivatives where in $(O)_n$, n=1. Route 4 is applicable primarily to the naphthalene derivatives of this invention, the synthesis of which can start with the known 6-hydroxy-2-acetonaphthone. Synthesis of the dibenzo[a,d]cycloheptene and dibenzo [b,e] oxepin acetic acid ester intermediates of this invention are by routes specific for those groups of compounds.

In Routes 1, 2, 3 and 4, R represents substituents at the 4-position of the 3-hydroxy-3-pyrroline-2,5-dione in formula (I) above.

The following examples, given by way of illustration and not to be construed as limiting, further clarify the invention.

Procedure for the Preparation of Substituted Naphthylacetophenones

The methyl ketone, 6-(3-hydroxy-3,4-dihydro-2H-1,5-benzodioxepin-3-ylmethoxy)-2-acetonaphthone, was prepared by the following route, starting with 6-hydroxy-2-acetonaphthone;

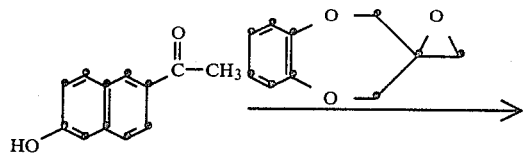

6-Loweralkoxy-2-acetonaphthones are prepared by reaction of 2-alkoxynaphthalenes with acetylchloride and aluminum trichloride under Friedel-Craft conditions.

EXAMPLE 1

Preparation of 6-(3-Hydroxy-3,4-dihydro-2H-1,5-benzodioxepin-3-ylmethoxy)-2-acetonaphthone A mixture of 6-hydroxy-2-acetonaphthone (186 mg, 1 mmole), 3,4-dihydro-2H-1,5-benzodioxepin-3-spirooxirane (178 mg, 1 mmole) and n-butanol (2 ml) containing 1 drop of detergent base (40% Triton B) in methanol was heated at 120° C. for 24 hours. An additional drop of detergent base solution was added and after another 24 hours, another drop of detergent base was added. After another 24 hours at 120° C., the mixture was evaporated to dryness, and the residue was purified by passing a solution in chloroform down a short column of silica gel (6 g). The eluate was evaporated to dryness and the residue crystallized from acetonitrile (~1 ml) to give 192 mg (53%) of product, mp 131°–132.5° C.

Analyzed for $C_{22}H_{20}O_5$ Required: C, 72.51; H, 5.53; Found: C, 72.54; H, 5.70.

General Procedure for the Preparation of Methyl Substituted Arylacetates (IV)

Route 4. Step 1

Substituted arylacetic acid esters (IV), were made by the oxidative rearrangement of the corresponding methyl ketones (III) by the method of E. C. Taylor and A. McKillop, *J. Amer. Chem. Soc.*, 93, 4919 (1971), ibid 95, 3340 (1973). Two examples of substituted arylacetic acid ester (IV) prepared by this process are set forth in Table I below.

TABLE I

| Compound IV | Yield % | MP °C. Solvent | Formula | Analysis Req. | Fd. |
|---|---|---|---|---|---|
| methyl 6-(3,4-dihydro-3-hydroxy-2H-1,5-benzodioxepin-3-ylmethoxy)-2-naphthylacetate | 61 | 106–108 diisopropyl ether | $C_{23}H_{22}O_6$ | C 70.04 H 5.62 | 70.30 5.87 |
| methyl 6-methoxy-2 naphthylacetate | 88 (crude) | 75–77 petroleum ether | $C_{14}H_{14}O_3$ | C 73.02 H 6.12 | 73.40 6.53 |

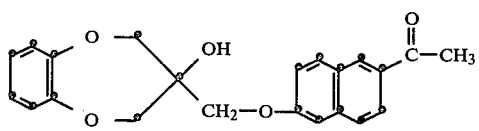

General Procedure for Preparing Aryloxyacetic Acid Esters

The general procedure for the preparation of aryloxyacetic acid ester derivatives is as follows:

The phenol intermediate (10 m mole) is added to a solution of sodium (10 m mole) in ethanol (20 ml) (i.e., sodium ethoxide) under nitrogen. To the cooled mixture is added ethyl (or methyl) bromoacetate (10 mmole) in ethanol (10 ml), and then the mixture is stirred for up to twelve hours at room temperature in order to complete the reaction. The ester is isolated by addition of water, extraction into chloroform and evaporation of the chloroform. The crude ester, in general, is sufficiently pure to be used directly in the amide forming step.

When 2-hydroxy-10,11-dihydro-5H-dibenzo-[a,d]cycloheptene is utilized as starting material in this reaction, there is obtained ethyl 10,11-dihydro-5H-dibenzo[a,d]cyclohepten-2-yloxyacetate.

When 3-hydroxy-10,11-dihydro-5H-dibenzo[a,d]cycloheptene is used as starting material in this reaction there is obtained ethyl 10,11-dihydro-5H-dibenzo[a,d]cyclohepten-3-yloxyacetate.

When 2-hydroxy-5H-5-oxodibenzo[a,d]cycloheptene is used as starting material in this reaction there is obtained ethyl-5H-5-oxodibenzo[a,d]cycloheptene-2-yloxyacetate.

amides (V) prepared by this process are set forth in Table II below.

TABLE II

| Compound | Yield % | MP °C. Solvent | Formula | Analysis Req. | Fd. |
|---|---|---|---|---|---|
| 6-(3,4-dihydro-3-hydroxy-2H-1,5-benzodioxepin-3-ylmethoxy)-2-naphthyl-acetamide | 62 | 201–202 MeOH | $C_{22}H_{21}NO_5$ | C 69.64 H 5.57 N 3.69 | 69.34 5.60 3. |
| 6-methoxy-2-naphthyl-acetamide | 55 | 242–245 DMF | $C_{13}H_{13}NO_2$ | C 72.54 H 6.08 N 6.50 | 72.71 6.30 6. |
| 10,11-dihydro-5-oxo-5H-dibenzo[a,d]cyclohepten-3-yloxyacetamide | 77 overall | 133–135 EtOAc | $C_{17}H_{15}NO_3$ | C 72.58 H 5.3 N 4.97 | 72.14 5.61 4.88 |
| 10,11-dihydro-5H-dibenzo[a,d]cyclohepten-3-yloxyacetamide | 59 overall | 147–150 MeOH | $C_{17}H_{17}NO_2$ | C 76.38 H 6.40 N 5.23 | 76.19 6.60 5.14 |

When 3-hydroxy-10,11-dihydro-5H-5-oxodibenzo[a,d]cycloheptene is utilized as starting material in this reaction there is obtained ethyl 10,11-dihydro-5H-5-oxodibenzo[a,d]cyclohepten-3-yloxyacetate.

When 2-hydroxy-6,11-dihydro-11-oxodibenz[b,e]oxepin is used as starting material for this reaction there is obtained ethyl 6,11-dihydro-11-oxodibenz[b,e]oxepin-2-yl-acetate.

When 4-hydroxy-6,11-dihydro-11-oxodibenz[b,e]oxepin is used as starting material for this reaction there is obtained ethyl 6,11-dihydro-11-oxodibenz[b,e]oxepin-4-ylacetate.

General Procedure for Preparing the Substituted Acetamides (V)

Route 2, Step 3

The substituted acetic acid esters (IV) are converted to the corresponding amides (V) by treatment with 7½ parts by weight of a saturated solution of ammonia in methanol at room temperature. Conversion to the amide is followed by thin layer chromatography and may require several days. Examples of substituted acet- When methyl (10,11-dihydro-5H-dibenzo[a,d]cyclohepten-5-on-2-yl)acetate is utilized as the starting material in this reaction there is obtained (10,11-dihydro-5H-dibenzo[a,d]cyclohepten-5-on-2-yl)acetamide.

When ethyl [(6,11-dihydro-11-oxodibenzo-[b,e]oxepin-2-yl)oxy]acetate is used as the starting material in this reaction, there is obtained [(6,11-dihydro-11-oxodibenzo[b,e]oxepin-2-yl)oxy]acetamide.

When ethyl 5H-5-oxodibenzo[a,d]cyclohepten-2-yloxyacetate is used as starting material in this reaction there is obtained 5H-5-oxodibenzo[a,d]cyclohepten-2-acetamide.

When ethyl 6,11-dihydro-11-oxodibenz[b,e]oxepin-4-ylacetate is used as starting material in this reaction there is obtained 6,11-dihydro-11-oxodibenz[b,e]oxepin-4-yl-acetamide.

EXAMPLE 2

General Method for the Preparation of 3-Hydroxy-4-substituted-3-pyrroline-2,5-diones from Acetamide Intermediates

Routes 1 and 2, Step 4

A mixture of the substituted acetamide (10 mmole), diethyl oxalate (1.533 g, 10.5 mmole) and dry dimethylformamide (20 ml) is stirred under nitrogen or argon and cooled in an ice-bath. Potassium t-butoxide (2.464 g, 22 mmole) is added in two equal portions 15 minutes apart and the reaction mixture is stirred for about 30 minutes in the ice-bath and then at room temperature overnight. The reaction mixture is poured into ice-water (100 ml). If the potassium salt of the product dissolves, the aqueous mixture is extracted with ethyl acetate (2×35 ml) and then acidified with 6 N hydrochloric acid in order to precipitate the product. The product is either collected by filtration or by extraction with ethyl acetate.

If the potassium salt is not soluble when the reaction mixture is quenched in ice-water, then it is necessary to acidify the resulting suspension and collect the product by filtration. The crude product is generally less pure when obtained in this way.

The compounds may be solvated after recrystallization (with either DMF, dioxane, isopropanol or acetonitrile) and require drying at 110° C./0.05 Torr in order to remove the solvate.

Examples of 3-hydroxy-4-substituted-3-pyrroline-2,5-diones prepared by this process are set forth in Table III below:

TABLE III

| Compound (I) | Yield % | MP °C. Solvent | Formula | Analysis Req. | Analysis Fd. |
|---|---|---|---|---|---|
| 3-hydroxy-4-[6-(3,4-dihydro-3-hydroxy-2H-1,5-dibenzoxepin-3-ylmethoxy)-2-naphthyl]-3-pyrroline-2,5-dione | 42 | 285–287 THF/MeCN | $C_{24}H_{19}NO_7$ | C 66.51<br>H 4.42<br>N 3.23 | 66.45<br>4.35<br>3.55 |
| 3-hydroxy-4-(11-oxo-6,11-dihydrodibenzo[b,e]oxepin-2-yl)-3-pyrroline-2,5-dione | 35 | 278–280 dec. EtOAc | $C_{18}H_{11}NO_5$ | C 67.29<br>H 3.45<br>N 4.36 | 67.11<br>3.40<br>3.90 |
| 3-hydroxy-4-(6-methoxy-2-naphthyl)-3-pyrroline-2,5-dione | 58 | 265–267 i-PrOH | $C_{15}H_{11}NO_4$ | C 66.91<br>H 4.11<br>N 5.20 | 67.0<br>4.31<br>5.36 |
| 3-hydroxy-4-(5-oxo-10,11-dihydrodibenzo[a,d]cyclohepten-3-yloxy)-3-pyrroline-2,5-dione dimethylformamide solvate | 58 | 115–117 EtOAc | $C_{19}H_{13}NO_5$·$C_3H_7NO$ | C 64.70<br>H 4.94<br>N 6.86 | 64.93<br>5.07<br>6.76 |

TABLE III-continued

| Compound (I) | Yield % | MP °C. Solvent | Formula | Analysis Req. | Fd. |
|---|---|---|---|---|---|
| 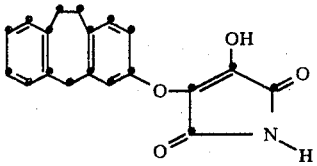<br>3-hydroxy-4-(10,11-dihydro-dibenzo[a,d]cyclohepten-3-yloxy)-3-pyrroline-2,5-dione | | toluene | $C_{19}H_{15}NO_4$.<br>1¼ $H_2O$ | C 66.37<br>H 5.12<br>N 4.07 | 66.71, 66.15<br>5.07, 5.39<br>3.91, 4.13 |

When (10,11-dihydro-5H-dibenzo[a,d]cyclohepten-5-on-2-yl)acetamide is employed as the starting amide there is obtained 4-(10,11-dihydro-5H-dibenzo[a,d]cyclohepten-5-on-2-yl)3-hydroxy-3-pyrroline-2,5-dione.

When [(6,11-dihydro-11-oxodibenzo[b,e]-oxepin-2-yl)oxy]acetamide is employed as the starting amide there is obtained 4-[(6,11-dihydro-11-oxodibenzo[b,e]oxepin-2-yl)oxy]-3-hydroxy-3-pyrroline-2,5-dione.

When 2-(5H-5-oxodibenzo[a,d]cyclohepten-5-on-3-yl)acetamide is employed as the starting material, there is obtained 4-(5H-5-oxodibenzo[a,d]cyclohepten-5-on-3-yl)-3-hydroxy-3-pyrroline-2,5-dione.

When 6,11-dihydro-11-oxodibenz[b,e]oxepin-4-ylacetamide is employed as starting material, there is obtained 4-(6,11-dihydro-11-oxodibenz[b,e]oxepin-4-yl)-3-hydroxy-3-pyrroline-2,5-dione.

General Method for the Preparation of 3-Hydroxy-4-Substituted-3-pyrroline-2,5-diones from Substituted Acetonitrile Intermediates A mixture of the substituted-acetonitrile (10 mmole), diethyl oxalate (1.53 g, 10.5 mmole) and dry dimethylformamide (20 ml) is stirred under nitrogen or argon and cooled in an ice-bath. Potassium t-butoxide (2.46 g, 22 mmole) is added in two equal portions 15 minutes apart and the reaction mixture is stirred for about 30 minutes in the ice-bath, and then overnight. Most of the dimethylformamide is evaporated in vacuo. To the residue is added water (50 ml) and ethyl acetate (100 ml). The mixture is made acidic (pH 4–5) with dilute hydrochloric acid. The ethyl acetate phase after washing with water, and drying (MgSO$_4$) is evaporated.

The residue is dissolved in cooled sulfuric acid (8 ml) and the solution allowed to stand at room temperature for 18 hours. The acid solution is poured onto ice, or mixed with 90% ethanol-H$_2$O (100 ml) to obtain the hydroxypyrrolinedione. The crude hydroxypyrrolinedione is recovered by filtration after the ice has melted (or evaporation of the ethanol from the ethanol-water mixture if the latter is used).

When 5H-dibenzo[a,d]cyclohepten-5-on-2-ylacetonitrile (J. Med. Chem. 20, 1557 (1977) is treated by the above procedure there is obtained 4-(5H-dibenzo[a,d]cyclohepten-5-on-2-yl)-3-hydroxy-3-pyrroline-2,5-dione.

When 7-chloro-5H-dibenzo[a,d]cyclohepten-5-on-2-ylacetonitrile is treated according to the above procedure there is obtained 4-(7-chloro-5H-dibenzo[a,d]cyclohepten-5-on-2-yl)-3-hydroxy-3-pyrroline-2,5-dione.

The 7-chloro-5H-dibenzo[a,d]cyclohepten-2-ylacetonitrile is prepared according to the procedure described in the above reference using methyl 5-chloro-2-methylbenzoate as starting material.

Preparation of Tricyclic Hydroxypyrrolinedione Derivatives where R$_1$, R$_2$=H,OH For preparation of tricyclichydroxypyrrolinedione derivatives in which the central carbon is substituted with a hydroxyl group the corresponding keto tricyclicacetamide intermediate is reduced using sodium borohydride in ethanol at 0°–50° C. The reduced amide intermediates are then reacted with diethyl oxalate and potassium t-butoxide in dimethylformamide to give the final hydroxypyrrolinedione derivatives (R$_1$, R$_2$=H,OH) according to the procedure of Example 2.

EXAMPLE 3

Preparation of 2-[(10,11-Dihydro-5-hydroxy-5H-dibenzo[a,d]cyclohepten-3-yl)oxy]acetamide Sodium borohydride (0.076 g, 2 mmole) is added in portions to a mixture of [(10,11-dihydro-5-oxo-5H-didibenzo[a,d]cyclohepten-3-yl)oxy]acetamide. (0.28 g, 1.0 mmole) in ethanol (40 ml) with stirring at room temperature. The mixture is stirred for 3 hours, and then the ethanol evaporated. The residue is slurried with water and filtered to give the above intermediate.

This intermediate when reacted with diethyl oxalate, potassium t-butoxide in dimethylformamide (as described in the general procedure of Example 2 for preparation of 4-substituted-3-hydroxy-3-pyrroline-2,5-diones from acetamide intermediates) gives 4-(10,11-dihydro-5-hydroxy-5H-dibenzo[a,d]cyclohepten-3-yl)-3-hydroxy-3-pyrroline-2,5-dione.

Included within the scope of the invention are the pharmaceutically acceptable salts of formula (I) compounds. The compounds of formula (I) are strong organic acids with a pKa in the range 2–4. These salts are readily formed with the usual inorganic cations such as sodium, potassium and ammonium. Salts with organic amines such as trimethylamine, triethylamine, n-butylamine and the like are also very stable. The neutralization can be carried out by a variety of procedures known to the art to be generally useful for the preparation of such salts. The choice of the most suitable procedure will depend on a variety of factors including convenience of operation, economic considerations, and particularly the solubility characteristics of the particular free base, the acid, and the acid addition salt.

The compounds of formula (I) are utilized for the stated utilities by formulating them in a composition such as tablet, capsule or elixir for oral administration. Sterile solutions or suspensions can be used for parenteral administration. About 10 to 200 mg of a compound of formula (I) or a physiologically acceptable vehicle, carrier, excipient, binder, preservative, stabilizer, flavor, etc., in a unit dosage form as called for by accepted pharmaceutical practice. The amount of active substance in the composition is such that dosage in the range indicated is obtained. The total daily dose will be in the 30 to 2000 mg range, preferably 50 to 1000 mg.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like, a lubricant such as magnesium stearate; a sweetening agent such as sucrose or lactose; a flavoring agent such as peppermint, oil of wintergreen or cherry. When the dosage unit form is a capsule, it may contain in addition to materials of the above type a liquid carrier such as a fatty oil. Various other materials may be present as coating or to otherwise enhance the pharmaceutical elegance of the preparation. For instance tablets may be coated with shellac, sugar or the like. A syrup or elixir may contain the active compound sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a conventional vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

What is claimed is:

1. A method of treating or preventing the formation of calcium oxalate kidney or bladder stones which comprises administering to a patient with or prone to renal lithiasis an effective amount of a compound having the structural formula:

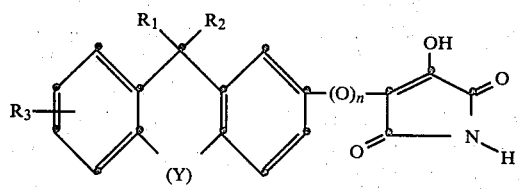

wherein:
n is 0 or 1;
Y is $CH_2-CH_2$; $CH=CH$; $CH_2-O$; $O-CH_2$;
$R_1$ and $R_2$ are both hydrogen, hydrogen and hydroxyl or taken together are $=O$;
$R_3$ is hydrogen, halogen or a pharmaceutically acceptable salt thereof.

2. The compounds having the structural formula:

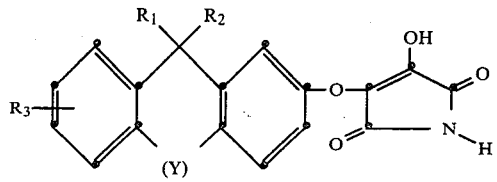

wherein
Y is $CH_2-CH_2$; $CH=CH$; $CH_2-O$; $O-CH_2$;
$R_1$ and $R_2$ are both hydrogen, hydrogen and hydroxyl or taken together are $=O$;
$R_3$ is hydrogen, halogen or a pharmaceutically acceptable salt thereof.

3. The compounds according to claim 2 wherein
Y is $CH_2-CH_2$; $CH=CH$;
$R_1$ and $R_2$ are both hydrogen, hydrogen and hydroxyl or taken together are $=O$;
$R_3$ is hydrogen or halogen;
having the structural formula:

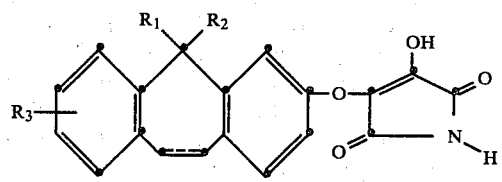

wherein the dotted line indicates saturation or unsaturation or a pharmaceutically acceptable salt thereof.

4. The compounds according to claim 2 wherein
Y is $CH_2-O$;
$R_1$ and $R_2$ are both hydrogen, hydrogen and hydroxyl or taken together are $=O$;
$R_3$ is hydrogen or halogen having the structure:

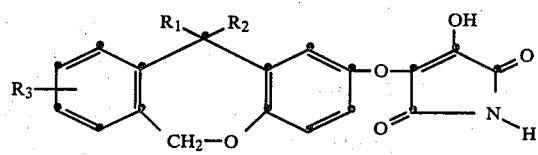

or a pharmaceutically acceptable salt thereof.

5. Compounds of claim 2 designated 3-hydroxy-4-[(10,11-dihydro-5-oxo-5H-dibenzo[a,d]cyclohepten-3-yl)-oxy]-3-pyrroline-2,5-dione and 3-hydroxy-4-[(10,11-dihydro-5H-dibenzo[a,d]cyclohepten-3-yl)oxy]-3-pyrroline-2,5-dione.

6. Compounds having the structural formula:

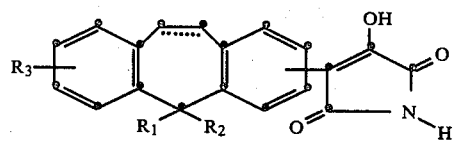

wherein $R_1$ and $R_2$ are both hydrogen, hydrogen and hydroxyl, or taken together are $=O$;
$R_3$ is hydrogen or halogen.

7. A compound of claim 6 which is 4-(5H-dibenzo[a,d]cyclohepten-5-on-2-yl)-3-hydroxy-3-pyrroline-2,5-dione.

8. A pharmaceutical composition useful in the treatment or prevention of the formation of calcium oxalate kidney or bladder stones comprising an effective amount of a compound of claim 2 or a pharmaceutically acceptable salt thereof and a pharmaceutically acceptable carrier.

9. A pharmaceutical composition useful in the treatment or prevention of the formation of calcium oxalate kidney or bladder stones comprising an effective amount of a compound of claim 6 or a pharmaceutically acceptable salt thereof and a pharmaceutically acceptable carrier.

* * * * *